(12) United States Patent
Tsuchiya et al.

(10) Patent No.: US 9,031,313 B2
(45) Date of Patent: May 12, 2015

(54) INSPECTION SYSTEM

(75) Inventors: Hideo Tsuchiya, Tokyo (JP); Fumio Ozaki, Kanagawa (JP)

(73) Assignees: NuFlare Technology, Inc., Numazu-shi (JP); Kabusiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 549 days.

(21) Appl. No.: 12/781,232

(22) Filed: May 17, 2010

(65) Prior Publication Data

US 2011/0044528 A1 Feb. 24, 2011

(30) Foreign Application Priority Data

Aug. 18, 2009 (JP) .................................. 2009-189605

(51) Int. Cl.
*G03F 1/84* (2012.01)
*G06T 7/00* (2006.01)
*G01N 21/956* (2006.01)

(52) U.S. Cl.
CPC . *G03F 1/84* (2013.01); *G06T 7/001* (2013.01); *G06T 2207/30148* (2013.01); *G01N 21/95607* (2013.01); *G01N 2021/95676* (2013.01)

(58) Field of Classification Search
CPC .. G03F 1/84; G06T 7/001; G06T 2207/30148
See application file for complete search history.

(56) References Cited

U.S. PATENT DOCUMENTS

| | | | |
|---|---|---|---|
| 6,990,225 B2 | 1/2006 | Tanaka et al. | |
| 7,271,891 B1 | 9/2007 | Xiong et al. | |
| 7,564,545 B2 | 7/2009 | Stokowski | |
| 8,139,841 B2 * | 3/2012 | Shibuya et al. | 382/141 |
| 8,781,212 B2 * | 7/2014 | Tsuchiya et al. | 382/149 |
| 2002/0019729 A1 * | 2/2002 | Chang et al. | 703/6 |
| 2004/0081350 A1 * | 4/2004 | Kitamura et al. | 382/149 |
| 2006/0036979 A1 | 2/2006 | Zurbrick et al. | |
| 2006/0239535 A1 * | 10/2006 | Takada et al. | 382/145 |
| 2007/0064997 A1 | 3/2007 | Itoh | |

(Continued)

FOREIGN PATENT DOCUMENTS

| | | |
|---|---|---|
| JP | 2000-258349 | 9/2000 |
| JP | 2001-516898 | 10/2001 |

(Continued)

OTHER PUBLICATIONS

U.S. Appl. No. 13/017,641, filed Jan. 31, 2011, Tsuchiya et al.

(Continued)

*Primary Examiner* — Asfand Sheikh
(74) *Attorney, Agent, or Firm* — Oblon, McClelland, Maier & Neustadt, L.L.P.

(57) ABSTRACT

The entire surface of a photomask 101 is inspected after data and parameters of the lithography simulator are set in the operation setting screen of a control computer 110 and after the inspection system 100 is calibrated. The coordinates of a portion or portions determined in the inspection to be a defect are written into an XML file. When the inspection system 100 is in the die-to-database inspection mode, the control computer 110 reads pattern data from the database, which data is used by the inspection system 100 to generate reference data, and then converts the read pattern data into OASIS format, which is highly versatile. The optical image captured by the inspection system 100 is converted into a bitmap. These data are sent to the lithography simulator, together with simulation operating conditions and the image data that was used to calibrate the inspection system 100.

6 Claims, 13 Drawing Sheets

(56) References Cited

U.S. PATENT DOCUMENTS

| | | | |
|---|---|---|---|
| 2007/0165938 A1* | 7/2007 | Matsumura et al. | 382/144 |
| 2009/0098472 A1* | 4/2009 | Morishita et al. | 430/30 |
| 2011/0044529 A1 | 2/2011 | Tsuchiya et al. | |
| 2011/0188734 A1* | 8/2011 | Tsuchiya et al. | 382/149 |
| 2012/0140060 A1* | 6/2012 | Tsuchiya et al. | 348/126 |

FOREIGN PATENT DOCUMENTS

| | | |
|---|---|---|
| JP | 2002-328462 | 11/2002 |
| JP | 2005-500671 | 1/2005 |
| JP | 2007-79423 | 3/2007 |
| JP | 2008-112178 | 5/2008 |
| JP | 2009-105430 | 5/2009 |
| WO | WO 99/14706 | 3/1999 |
| WO | WO 02/075793 A2 | 9/2002 |

OTHER PUBLICATIONS

Office Action issued May 6, 2011, in Japanese Patent Application No. 2009-189605 with English translation.

U.S. Appl. No. 13/307,389, filed Nov. 30, 2011, Tsuchiya et al.

Combined Taiwanese Office Action and Search Report issued Jun. 17, 2013 in Patent Application No. 099115936 with English Translation.

* cited by examiner

Fig. 7

Setting Screen of Simulator Operating Conditions

Setting of Inspection System

| Designation of Inspection Mode | ◆ D-D  ◇ D-DB |
| --- | --- |
| Transfer Mode to Simulator | After Completion of Inspection of One Mask ▶ |
| Name of Mask | ABC_POLY |
| Type of Mask | ◇ Cr  ◆ ArF-HT |
| File Name of Database | ABC_POLY.draw |

Setting of Simulator

| IP Adress | 192.168.1.64 |
| --- | --- |
| User ID | sim_user1 |
| Login Password | ******** |
| Designation of Lithograpy Conditions | POLY_45 ▶ |
| Determination Conditions | detect_45_hhh ▶ |

Detailed Lithography Condition Setting

| Type of Condition | Designation Items and Setting Values ||||
| --- | --- | --- | --- | --- |
|  | Wavelength of Light Source for Transfer | Pattern Feature of Light Source for Transfer | Diaphragm Value of Light Source for Transfer | Type of Resist |
| POLY_45 | 193 | Qu | 0.8 | EAA |
| CONTACT_45 | 193 | C | 0.9 | DDD |
| METAL_32 | 193 | P | 0.75 | FFA |
| ~ | | | | |

Detailed Determination Conditions Setting

| Type of Condition | Determination Items and Threshold Values ||||
| --- | --- | --- | --- | --- |
|  | Line Width Defects | Position Displacement | Approach Distance to Adjacent Pattern Feature | Constriction of Pattern Feature |
| detect_45_hhh | 8 | 8 | 8 | 8 |
| detect_45_ppp | 9 | 9 | 9 | 10 |
| test_32_xxx | 4 | 6 | 6 | 4 |
| ~ | | | | |

INSPECTION SYSTEM

BACKGROUND OF THE INVENTION

1. Field of the Invention

The present invention relates to an inspection system, and more particularly to an inspection system used to detect defects of the pattern formed on an object to be inspected, such as a mask.

2. Background Art

In recent years, as the levels of integration and capacity of large scale integrated circuits (LSIs) increase, there has been a need to continue to reduce the width of the circuit patterns of semiconductor devices. Semiconductor devices are manufactured by a reduced projection exposure apparatus called a "stepper" using original artwork patterns with a circuit pattern formed thereon, that is, masks or reticles (hereinafter referred to collectively as masks). Specifically, the pattern on a mask is transferred to the wafer by exposure to light, thereby forming circuits on the wafer. Masks used to transfer such fine circuit patterns to the wafer are manufactured by electron beam writing apparatuses, which can write micropatterns. Further, effort has been made to develop a laser beam writing apparatus, which uses a laser beam for writing. It should be noted that electron beam apparatuses are also used to directly write a circuit pattern on a wafer.

Incidentally, since the cost to manufacture LSIs is very high, the increase of the yield is required to make the manufacture economically feasible. However, the dimensions of the patterns for LSI devices, as typified by 1-gigabit class DRAMs (random access memories), are about to be scaled down from the order of submicrons to the order of nanometers. A major cause of loss in yield is due to defects of a mask pattern. Further, since there has been a decrease in the dimensions of LSI patterns formed on semiconductor wafers, the size of pattern defects to be detected is very small. Therefore, high inspection accuracy is required of inspection systems for detecting defects of transfer masks used in LSI manufacture.

There are two known mask defect detecting methods: the die-to-die inspection method and the die-to-database inspection method. The die-to-die inspection method is used when the mask to be inspected has thereon a plurality of identical chip patterns, or a plurality of chip patterns each including an identical pattern segment. In this method, these identical chip patterns or identical pattern segments, which are to be transferred to the wafer, are compared to each other. This method permits accurate inspection using a relatively simple system configuration, since patterns on the same mask are directly compared to each other. However, this method cannot detect a defect common to both compared patterns. In the die-to-database inspection method, on the other hand, an actual pattern on a mask is compared to reference data generated from the design pattern data that was used to manufacture the mask. Thus, this method allows exact comparison of the pattern with the design pattern data, although the required system size is large since the method requires a processing system for generating a reference image. There is no choice but to use this inspection method when the mask to be inspected has only one chip pattern to be transferred to the wafer.

In die-to-die inspection system, light is emitted from a light source, and the mask to be inspected is irradiated with this light through an optical system. The mask is mounted on a table, and this table is moved so that the emitted beam of light scans the surface of the mask. Light transmitted through or reflected from the mask are acquired by image sensors, thereby forming an image thereon. The optical image thus formed on the image sensor is sent to a comparing unit as measurement data. The comparing unit compares the measurement data with reference data in accordance with an appropriate algorithm, and if they are riot identical, the mask is determined to have a defect (see, e.g., Japanese Laid-Open Patent Publication No. 2008-112178).

Conventional inspection systems are so designed as to complete a defect evaluation process (i.e., a process of determining whether the size of a detected defect is within the tolerable range) in a time approximately equal to the time required to capture an optical image of the mask by the image sensor. Specifically, each inspection system includes a defect evaluation processing unit that matches the scale of the defect evaluation process expected to be performed. However, as pattern dimensions have been scaled down, the scale of the defect evaluation process has been increased to such an extent that the time required for the process is too long as compared to the time required to capture an optical image of the mask.

Incidentally, it is not necessary to accurately control the dimensions, etc. of all the patterns formed on a mask. For example, a dummy feature or pattern, which does not serve for wiring purposes, is sometimes formed in a place where the pattern density is extremely low. No problem is presented even if this dummy feature or pattern has some "pin-hole defect" or edge roughness.

On the other hand, it is necessary to accurately control the impedance of a pattern through which a clock signal passes (i.e., a clock line), and the position and the diameter of a contact hole passing through a plurality of layers.

In order to address this problem, a method has been proposed in which the level of importance, or weight, of each pattern is added to design pattern data as pattern importance information, and pattern data and pattern importance information are input to the inspection system. For example, Japanese Laid-Open Patent Publication No. 2009-105430 discloses a method for simulating a lithographic design comprised of a number of polygons arranged in a predetermined configuration. Specifically, referring to FIG. 4 of this publication, an aerial image is generated using a bitmap image available from the polygon design database (box 126), and resist modeling or simulation is performed using this aerial image (box 128).

Further, Published Japanese Translation of PCT Application No. 2001-516898 states as follows: "In any mask inspection system, the important decision to make is whether a given defect will 'print' on the underlying photoresist in a lithography process under specified conditions. If a mask defect does not print or have other effect on the lithography process, then the mask with the defect can still be used to provide acceptable lithography results. Therefore, one can avoid the expense in time and money of repairing and/or replacing masks whose defects do not print." This publication discloses a method of receiving a defect area image including an image of a portion of a mask and generating a simulated image. This simulated image includes a simulation of an image which would be printed on the wafer.

However, if such a method is performed within the inspection system, an increase in the scale of the defect evaluation process results. Further, although in the method of the above PCT publication the lithography simulation is performed by a simulator in the inspection system, it will be understood that the simulation may be carried out by a general purpose simulator, which is convenient in use. It should be noted that some simulators cannot perform resist modeling or simulation although they can generate an aerial image of a wafer. That is, these simulators can perform basic simulation, but not higher level simulation. It is disadvantageous that the type of simulator used restricts the information that can be obtained.

It is, therefore, an object of the present invention to provide an inspection system capable of facilitating defect evaluation and capable of performing a defect evaluation process in conjunction with a highly versatile simulator.

Other challenges and advantages of the present invention are apparent from the following description.

SUMMARY OF THE INVENTION

According to one aspect of the present invention, an inspection system comprises an optical image capture unit configured to capture optical images of an object to be inspected by irradiating the object with light, comparing unit configured to compare the optical images, and an interface unit configured to output to a lithography simulator the optical images and the coordinates of a portion determined to be a defect by the comparison, wherein the optical images and the coordinates of the portion together form a first inspection result.

According to another aspect of the present invention, an inspection system comprises an optical image capture unit configured to capture an optical image of an object to be inspected by irradiating the object with light, a reference image generating unit configured to generate a reference image from design data of the object to be inspected, a comparing unit configured to compare the optical image with the reference image, and an interface unit configured to output to a lithography simulator the optical image, reference data newly generated from the design data, and the coordinates of a portion determined to be a defect by the comparison, wherein the optical image, the reference data, and the coordinates of the portion together form a first inspection result.

BRIEF DESCRIPTION OF THE DRAWINGS

FIG. 7 shows an exemplary operation setting screen of the control computer in the inspection system.

DETAILED DESCRIPTION OF THE EMBODIMENTS

Figure 1:
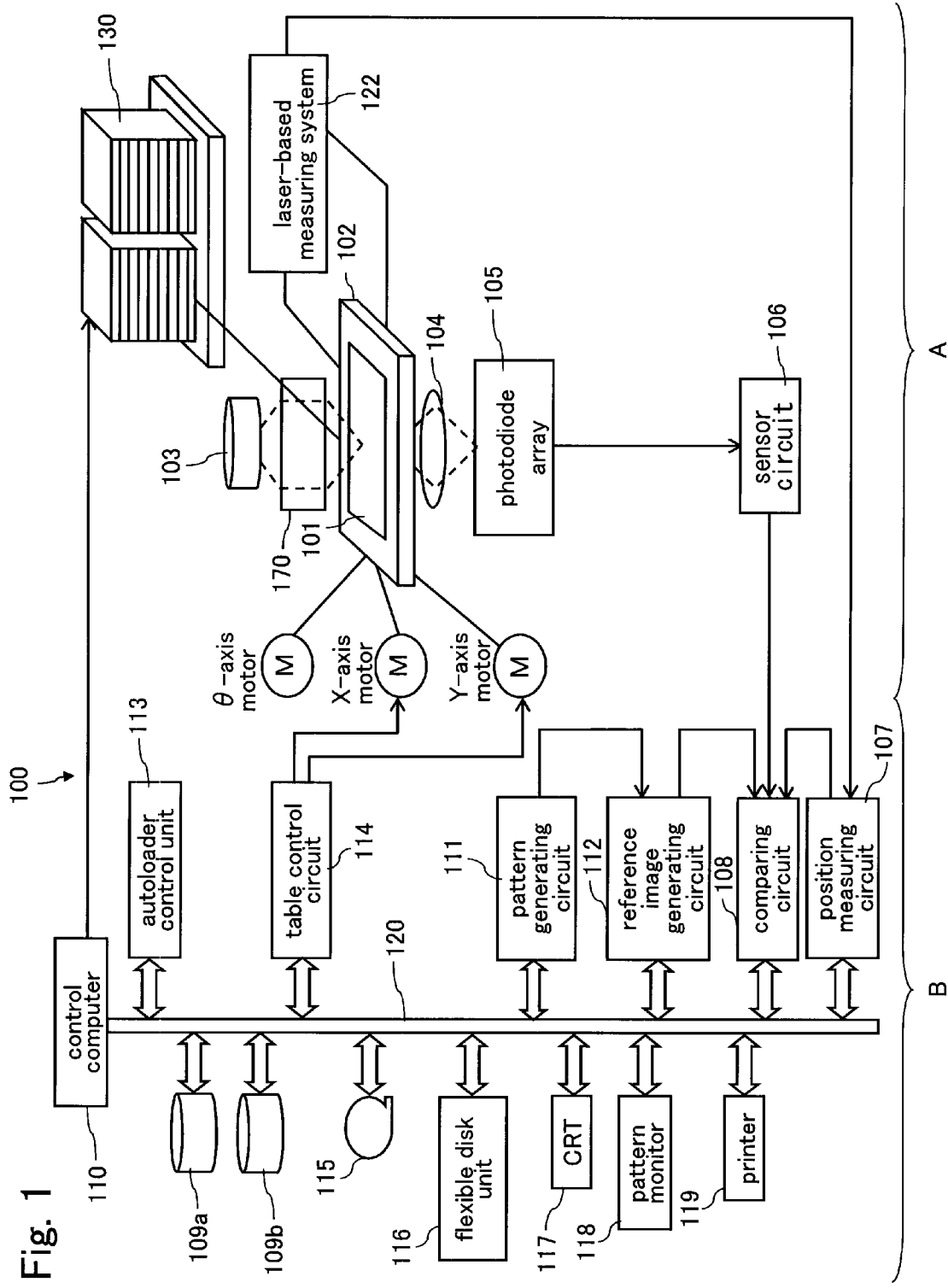
FIG. 1 is a diagram showing the configuration of an inspection system according to an embodiment of the present invention.

FIG. 1 is a diagram showing the configuration of an inspection system according to an embodiment of the present invention. Although the inspection system of the present embodiment will be described in connection with the inspection of masks used in photolithography, it is to be understood that the system may be used to inspect wafers.

As shown in FIG. 1, the inspection system 100 includes an optical image capture unit A and a control unit B.

The optical image capture unit A includes a light source 103, an XYθ table 102 movable in the horizontal X and Y directions and rotatable in a horizontal plane (or in a θ direction), an illumination optical system 170 serving as a transmission illumination system, an enlarging optical system 104, a photodiode array 105, a sensor circuit 106, a laser-based measuring system 122, and an autoloader 130.

In the control unit B, a control computer 110 which controls the entire inspection system 100 is connected through a bus 120 (serving as a data transmission path) to a position measuring circuit 107, a comparing circuit 108, a reference image generating circuit 112, a pattern generating circuit 111, an autoloader control unit 113, a table control circuit 114, a first magnetic disk unit 109a and a second magnetic disk unit 109b serving as storage units, a magnetic tape unit 115, a flexible disk unit 116, a CRT 117, a pattern monitor 118, and a printer 119. The XYθ table 102 is driven by X-, Y-, and θ-axis motors controlled by the table control circuit 114. These motors may be, e.g., step motors.

Design pattern data which is used as reference data in die-to-database inspection is stored in the first magnetic disk unit 109a. This data is read out and sent to the pattern generating circuit 111 when necessary in the course of the inspection process. The pattern generating circuit 111 converts the design pattern data into image data (or bit pattern data). This image data is then sent to the reference image generating circuit 112 for generation of reference data.

It should be noted that the inspection system of the present embodiment may include, in addition to the components shown in FIG. 1 described above, other known components required to inspect masks. Further, although the present embodiment is described in connection with the die-to-database inspection method, it is to be understood that the embodiment may be applied to the die-to-die inspection method. In such a case, an optical image of one of two separate identical patterns on the mask is treated as a reference image.

Figure 2:
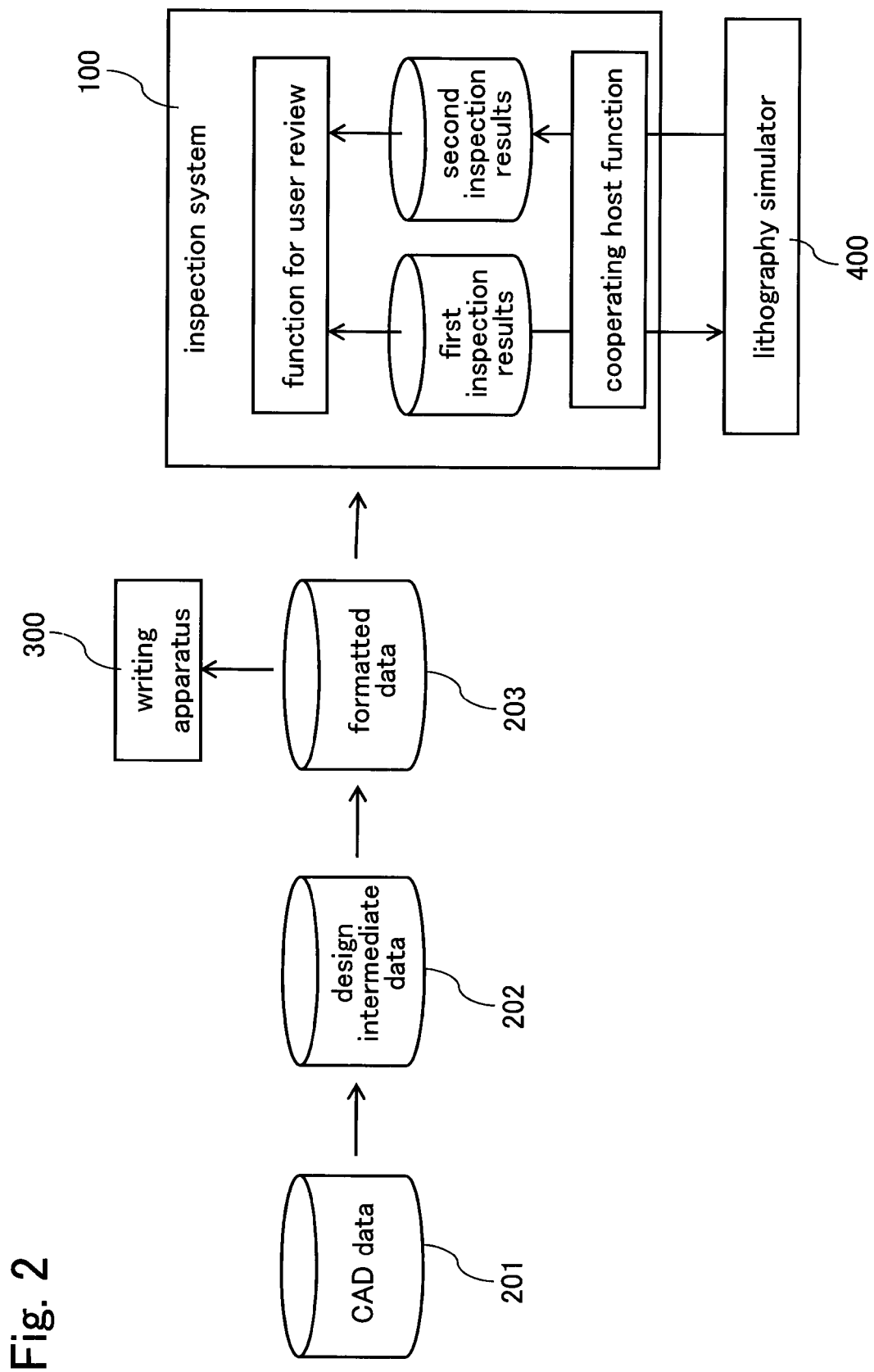
FIG. 2 is a schematic diagram showing a flow of data according to the present embodiment.

FIG. 2 is a schematic diagram showing a flow of data according to the present embodiment.

As shown in FIG. 2, CAD data 201 prepared by the designer (or user) is converted to design intermediate data 202 in a hierarchical format such as OASIS. The design intermediate data 202 includes data of the pattern formed on the mask created for each layer. It should be noted that, generally, writing apparatuses are not adapted to be able to directly read OASIS data. That is, each manufacturer of writing apparatus uses different data format. Therefore, OASIS data is converted, for each layer, to data 203 in a format specific to the writing apparatus 300 used, and this formatted data 203 is input to the writing apparatus 300. Likewise, the inspection system 100 is also not adapted to be able to directly read OASIS data, and therefore receives the formatted data 203 compatible with the writing apparatus 300. It should be noted that the inspection system 100 may receive converted or formatted data in a format specific to the system.

Incidentally, the formatted data for the writing or inspection (or the original OASIS data before it is converted into these formatted data) includes data of features for forming complicated pattern shapes provided to accurately control the line width and spacing of patterns written on the mask, as well as to accurately control the line width and spacing of dummy patterns formed to improve the resolution of the actual patterns. The volume of the resulting pattern data is huge, and therefore the writing apparatus and the inspection system are adapted to prevent a delay in the writing time and in the inspection time due to the increased volume of the pattern data. Specifically, the function to read pattern data and expand it is performed by a high speed, high capacity parallel processing computer in combination with a hard disk unit designed to accommodate the read rate required for the processing.

Figure 3:
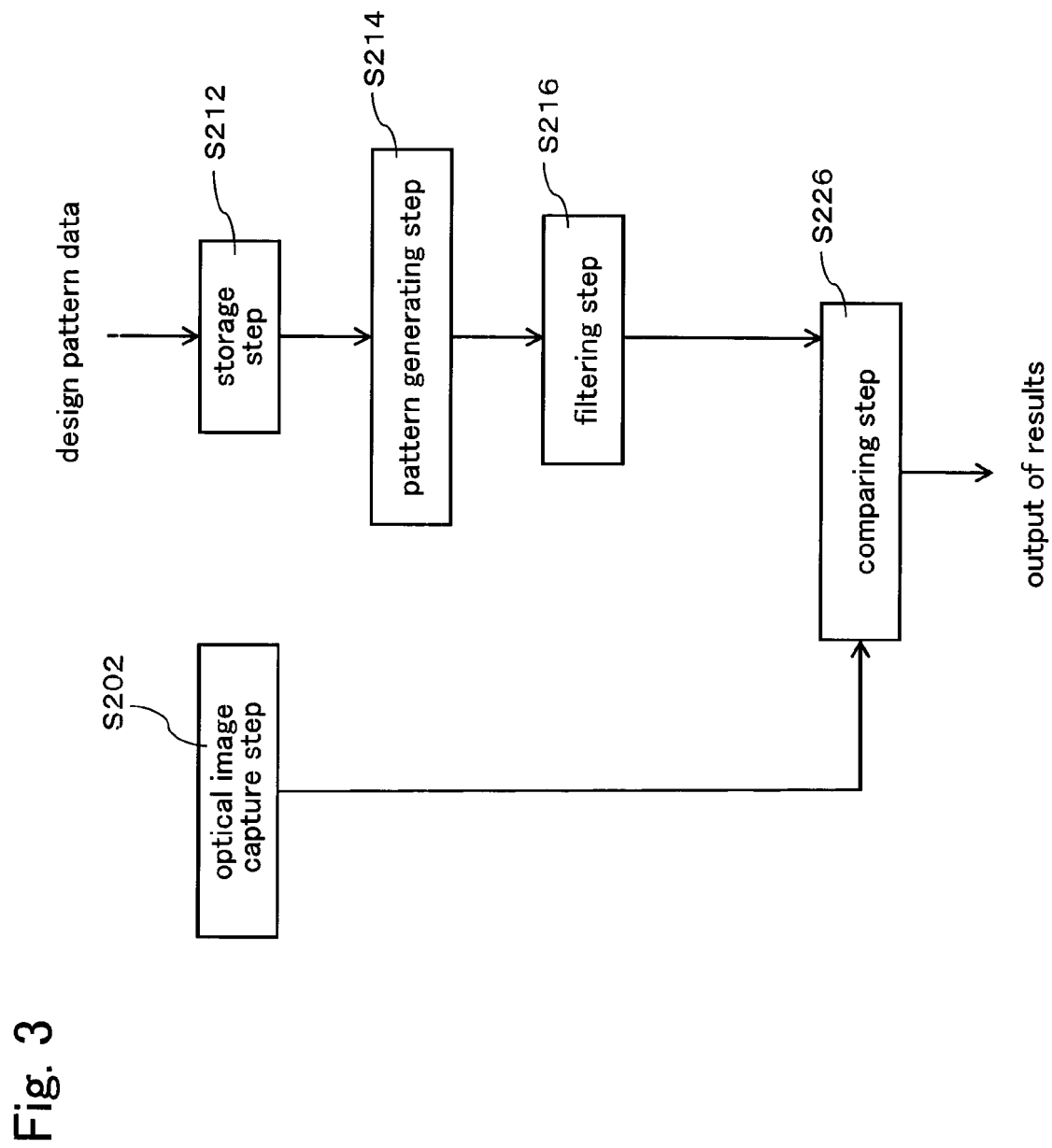
FIG. 3 is a flowchart showing an inspection process.

FIG. 3 is a flowchart showing an inspection process.

As shown in FIG. 3, this inspection process includes an optical image capture step (S202), a design pattern data storage step (S212), an pattern generating step (S214), a filtering step (S216), and a comparing step (S226), where the pattern generating step and the filtering step together form a design image data generating step.

At the optical image capture step S202, the optical image capture unit A shown in FIG. 1 captures an optical image (measurement data) of a photomask 101. It will be noted that this optical image includes an image of a pattern on the mask, which pattern was written in accordance with the corresponding design pattern data. The detailed method of capturing this optical image is, e.g., as follows.

The photomask 101 serving as an inspection workpiece is mounted on the XYθ table 102 provided to be movable in two horizontal directions by X- and Y-axis motors and rotatable in a horizontal plane by a θ-axis motor. The pattern formed on the photomask 101 is then irradiated with light emitted from the light source 103 disposed above the XYθ table 102. More specifically, the beam of light emitted from the light source 103 passes through the illumination optical system 170 and shines on the photomask 101. The enlarging optical system 104, the photodiode array 105, and the sensor circuit 106 are disposed below the photomask 101. The light transmitted through the photomask 101 passes through the enlarging optical system 104 and reaches the photodiode array 105, thereby forming an optical image thereon. It should be noted that the enlarging optical system 104 may have its focus automatically adjusted by an autofocus mechanism (not shown). Further, though not shown, the inspection system 100 may be constructed such that light is also emitted from a source below the photomask 101, and the reflected light is passed through an enlarging optical system to a second photodiode array, thus capturing the transmitted light and the reflected light simultaneously.

Figure 4:
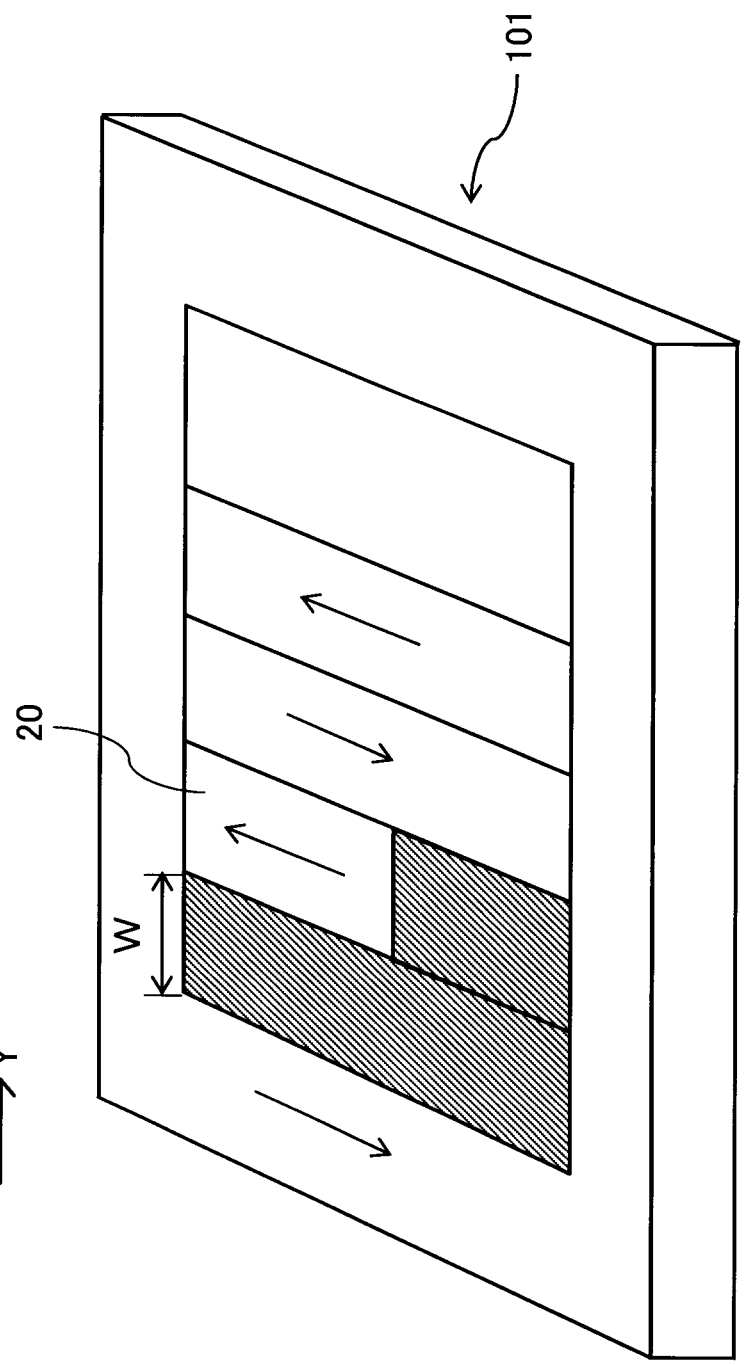
FIG. 4 is a diagram illustrating the way in which an optical image is captured.

FIG. 4 is a diagram illustrating the way in which an optical image is captured.

The inspection area is divided into a plurality of strip-shaped inspection stripes 20 by imaginary lines running in the X direction, where the width of each inspection stripe 20 in the Y direction is equal to the scan width W, as shown in FIG. 4. The movement of the XYθ table 102 is controlled so that each inspection stripe 20 is continuously scanned in the negative or positive X direction with the light to capture an image of the inspection stripe. At that time, the photodiode array 105 continuously generates an image (of each inspection stripe 20) having a width corresponding to the scan width W, as shown in FIG. 4. After capturing an image of the first inspection stripe 20 by scanning it, e.g., in the negative X direction, the second inspection stripe 20 is continuously scanned in the positive (i.e., opposite) X direction to capture an image of a width corresponding to the scan width W. Likewise, the third inspection stripe 20 is scanned in the negative x direction (opposite the direction in which the second inspection stripe 20 is scanned) to capture an image. This way of continuously capturing an image of one inspection stripe 20 after another reduces waste of processing time.

The pattern image formed on the photodiode array 105 is photoelectrically converted by the array 105 and A/D (analog to digital) converted by the sensor circuit 106. The photodiode array 105 is made up of sensors arranged in an array. These sensors may be, e.g., TDI (Time Delay Integration) sensors. Thus, the pattern on the photomask 101 is imaged by these TDI sensors while the XYθ table 102 is continuously moved in the positive or negative X direction. It will be noted that the light source 103, the enlarging optical system 104, the photodiode array 105, and the sensor circuit 106 together form a high power inspection optical system.

The XYθ table 102 can be moved in the X and Y directions and rotated in a θ direction (or in an XY plane) by a drive system such as a 3-axis (X-Y-θ) motor driven by the table control circuit 114 under the control of the control computer 110. These X-, Y-, and θ-axis motors may be, e.g., step motors. The position of the XYθ table 102 is measured by the laser-based measuring system 122, and the measurement data is sent to the position measuring circuit 107. Further, the photomask 101 is automatically loaded onto the XYθ table 102 from the autoloader 130 driven by the autoloader control circuit 113, and, upon completion of its inspection, the photomask 101 is automatically retrieved from the XYθ table 102.

The measurement data (representing an optical image) output from the sensor circuit 106 is sent to the comparing circuit 108, together with data indicative of the position of the photomask 101 on the XYθ table 102, which data is output from the position measuring circuit 107. The measurement data is, e.g., unsigned 8-bit data, representing the gray scale of each pixel.

At the storage step S212, the design pattern data that was used to form the pattern on the photomask 101 is stored in the first magnetic disk unit 109a serving as a storage unit.

The designed pattern includes pattern features each consisting of basic features such as rectangles and triangles. The first magnetic disk unit 109a stores feature data indicating the shape, size, and position of each pattern feature, specifically, e.g., information such as the coordinates (x, y) of the reference position of each feature, the length of its sides, and a shape code (or identifier) identifying the type of shape such as a rectangle or triangle.

Further, a group of pattern features defined in an area of approximately a few tens of micrometers square is referred to as a "cluster" or "cell." It is common practice that the design pattern data is defined in a hierarchical structure using clusters or cells. A cluster (or cell), which contains a pattern feature or features, may be used alone or repeated at certain intervals. In the former case the coordinate positions of the cluster (or cell) on the photomask are specified, whereas in the latter case the coordinate positions of each copy of the cluster (or cell) are indicated together with a repetition instruction. Each cluster (or cell) is disposed in a strip-shaped region, referred to as a "frame" or "stripe", having a width of a few hundreds of micrometers and a length of approximately 100 mm which corresponds to the length of the photomask in the X or Y direction.

At the pattern generating step S214, the pattern generating circuit 111 shown in FIG. 1 reads design pattern data of the photomask 101 from the first magnetic disk unit 109a through the control computer 110 and converts it into 2-bit or other multiple-bit image data (bit pattern data). This image data is sent to the reference image generating circuit 112.

Specifically, upon reading the design pattern data (serving as feature data), the pattern generating circuit 111 expands it to produce data of each pattern feature, and interprets the shape code in the data indicative of the shape of the pattern feature and obtains its dimensions. The pattern generating circuit 111 then divides the pattern into an imaginary grid of squares (or grid elements) having predetermined quantization dimensions, and produces 2-bit or other multiple-bit design image data of the design pattern segment in each grid element. By using the produced design image data, the pattern generating circuit 111 calculates the design pattern occupancy in each grid element (corresponding to a sensor pixel). This pattern occupancy in each pixel represents the pixel value.

At the filtering step S216, after receiving the design image data (i.e., image data of the pattern), the reference image generating circuit 112 performs appropriate filtering on the data.

Figure 5:
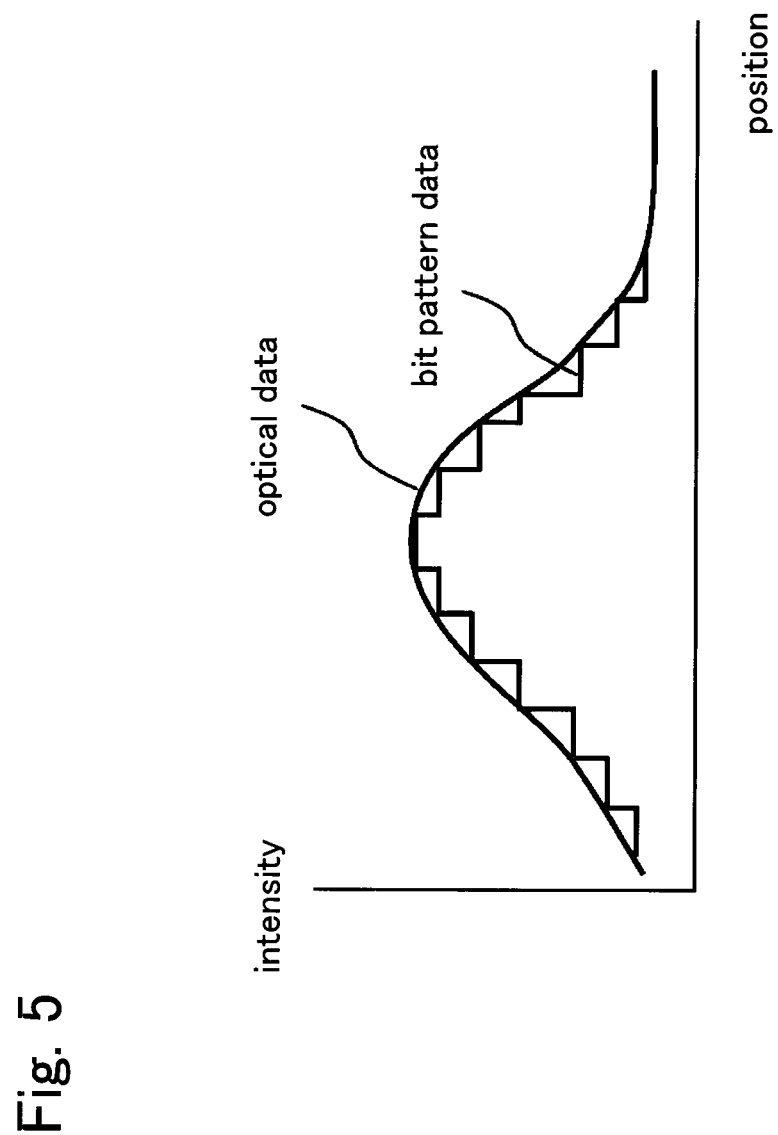
FIG. 5 is a diagram illustrating the filtering.

FIG. 5 is a diagram illustrating the filtering.

The optical image (or the measurement data representing it) output from the sensor circuit 106 is somewhat "blurred" due to the resolution characteristics of the enlarging optical system 104 and due to the aperture effect in the photodiode array 105, that is, this optical image is a spatially low-pass filtered image. Therefore, since the design image data corresponding to the optical image is digital data consisting of digital values representing the intensity (or gray scale) of each point of the image, this design image data may be filtered to match the "blurred" optical image, or measurement data. In this way, a reference image to be compared with the optical image is produced.

The measurement data is sent to the comparing circuit 108, as described above. The design pattern data, on the other hand, is converted into design image data by the pattern generating circuit 111 and the reference image generating circuit 112, and then also sent to the comparing circuit 108.

The comparing circuit 108 compares each portion of the optical image received from the sensor circuit 106 with the corresponding portion of the reference image generated by the reference image generating circuit 112 in accordance with a suitable comparison determination algorithm, and if the difference (e.g., in dimension) between these portions exceeds a predetermined value, the comparing circuit 108 determines that the portion of the optical image is a defect. The optical image to be compared may be a transmitted image or a reflected image or a combination thereof, and the algorithm is selected to be suitable for the image to be compared. If it is determined from the comparison that a portion of the optical image is a defect, then the coordinates of that portion and the optical image (imaged by the sensor) and the reference image, on which the detection of the defect is based, are stored as first inspection results.

Incidentally, defects associated with micropatterns include not only shape defects typified by pattern edge roughness, but also pattern line width defects and spacing defects between adjacent patterns due to pattern displacement, which are becoming more and more significant. Therefore, there has been an extremely strong need to accurately control the dimensions of patterns, thus increasing the difficulty of manufacturing masks. As a result, there has been loss in the yield of masks that meet required specifications, thereby raising mask manufacturing cost. In order to address this problem, a defect evaluating method has been proposed which uses a lithography simulator. This method simulates the image which would be printed from the mask to a wafer by the photolithography apparatus and determines whether or not the pattern on the mask is defective by inspecting the simulated image.

The inspection system 100 of the present embodiment has an interface unit through which data can be exchanged with a lithography simulator (also referred to as a process simulator) which is an external device. This allows the inspection system 100 to send the first inspection results and information necessary for lithography simulation to the lithography simulator 400, as shown in FIG. 2.

The control computer 110 in the inspection system 100 has a cooperating host function to work in conjunction with the lithography simulator 400. When the inspection system 100 instructs, using the cooperating host function, the lithography simulator 400 to start its operation, the lithography simulator 400 simulates the aerial image or resist image of a wafer based on information received from the inspection system 100. Specifically, the lithography simulator 400 simulates, based on the optical images obtained by the inspection system 100, the aerial image or resist image of a wafer to which pattern formed on the mask has been printed by the photolithography apparatus.

For example, in die-to-die inspection, two or more separate corresponding (or supposedly identical) patterns on the mask are compared to each other to determine the difference (e.g., in dimension) between them. The inspection system then sends to the lithography simulator two images: a sensor image including an image of a pattern defect found in the inspection by the system and the corresponding reference sensor image. The lithography simulator then simulates the aerial image or the resist image of a wafer to which the pattern on the mask has been printed under predetermined stepper illumination conditions and lithography conditions. In die-to-database inspection, on the other hand, the inspection system sends to the lithography simulator a sensor image including an image of a pattern defect found in the inspection by the system and the corresponding reference data generated from the design pattern data. It should be noted that this reference data is different from the reference image data which is also generated from the design pattern data but which is compared with the optical image by the comparing circuit 108. This reference data is newly generated for use by the simulator. For example, the only data required to visually recognize an area of the pattern around the defect may be extracted from the design pattern data and sent to the lithography simulator as the new reference data.

Figure 6B:
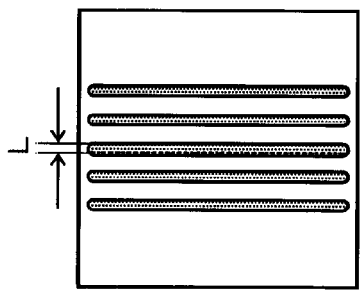
FIGS. 6A to 6D show exemplary types of defects.
Figure 6D:
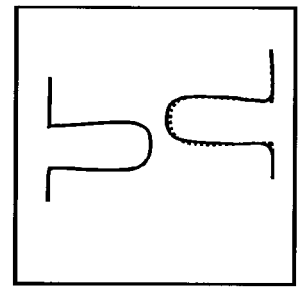
Figure 6A:
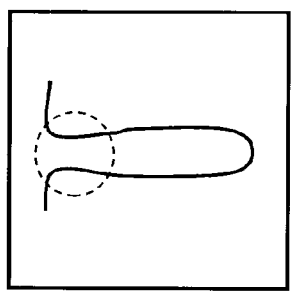
Figure 6C:
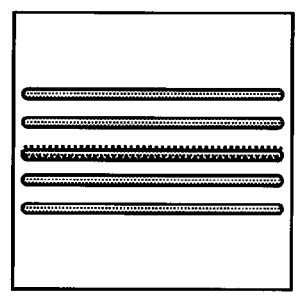

The lithography simulator 400 then generates simulated images based on the sensor image including the image of the pattern defect and based on the reference sensor image, and compares these simulated images to evaluate the defect. FIGS. 6A to 6D show exemplary types of defects. In FIG. 6A, a portion (enclosed by the dashed line) of a pattern feature is constricted. FIG. 6B shows a pattern having a line width larger than a predetermined width L. FIG. 6C shows a pattern displaced from its predetermined position (indicated by the dashed line). In FIG. 6D, a pattern feature is displaced from its predetermined position (indicated by the dashed line), and as a result is close to an adjacent pattern feature. For example, when a pattern having one of these defects is found in inspection by the inspection system, the lithography simulator makes two simulations. Specifically, the lithography simulator simulates, based on the sensor image of the "defective" pattern, the aerial image or resist image of a wafer to which the "defective" pattern has been printed, and also simulates, based on reference data of the corresponding reference pattern, the aerial image or resist image of the same wafer but to which, instead of the "defective" pattern, the reference pattern has been printed. The lithography simulator compares the two simulated images, and if the difference (e.g., in dimension) between these images exceeds a predetermined threshold value, the simulator determines that the defect of the "defective" pattern cannot be tolerated.

FIG. 7 shows an exemplary operation setting screen of the control computer 110 in the inspection system 100. The cooperating host function of the control computer 110 reads the operating conditions indicated by this screen and issues an operational instruction to the lithography simulator 400. It should be noted that in the setting screen, data and parameters of both the inspection system 100 and the lithography simulator 400 are set, as shown in FIG. 7, to allow the inspection system 100 and the lithography simulator 400 to work in conjunction with each other.

For example, referring to FIG. 7, when the inspection mode is set to be "D-DB," the control computer 110 reads pattern data (or pattern writing data) from the database, which data is used by the inspection system 100 to generate reference data. The control computer 110 then converts the read data into OASIS format, which is highly versatile, and outputs it to the lithography simulator 400.

The inspection system 100 may be connected to the lithography simulator 400 via a general network. For example, they may transmit data in accordance with the file transfer protocol (FTP), etc. In this case, for example, a network address, a user ID, a login password, etc. must be set before transmitting data.

The Detailed Lithography Conditions Setting box in the setting screen shown in FIG. 7 is where the user sets lithography conditions which are used by the lithograph simulator 400 to simulate the aerial image or the resist image of a wafer to which the pattern formed on the mask has been printed by the photolithography apparatus. Further, the Detailed Determination Conditions Setting box is where the user sets conditions for determining, based on simulated images, whether a pattern defect found in the inspection can be tolerated.

The operation results from the lithography simulator 400 are sent back to the inspection system 100 through the general communications network, as shown in FIG. 2. Receiving the operation results, the inspection system 100 inspects a different optical image of the pattern than that used in the first inspection and produces second inspection results, where this different optical image is selected based on the received operation results, taking into account the image that would be printed to a wafer.

The inspection system 100 has a function to display the first and second inspection results for user review, as shown in FIG. 2. This allows the operator to review defects based on the first and second inspection results. In this review process, the operator determines whether a pattern defect found in the inspection can be tolerated.

Figure 8:
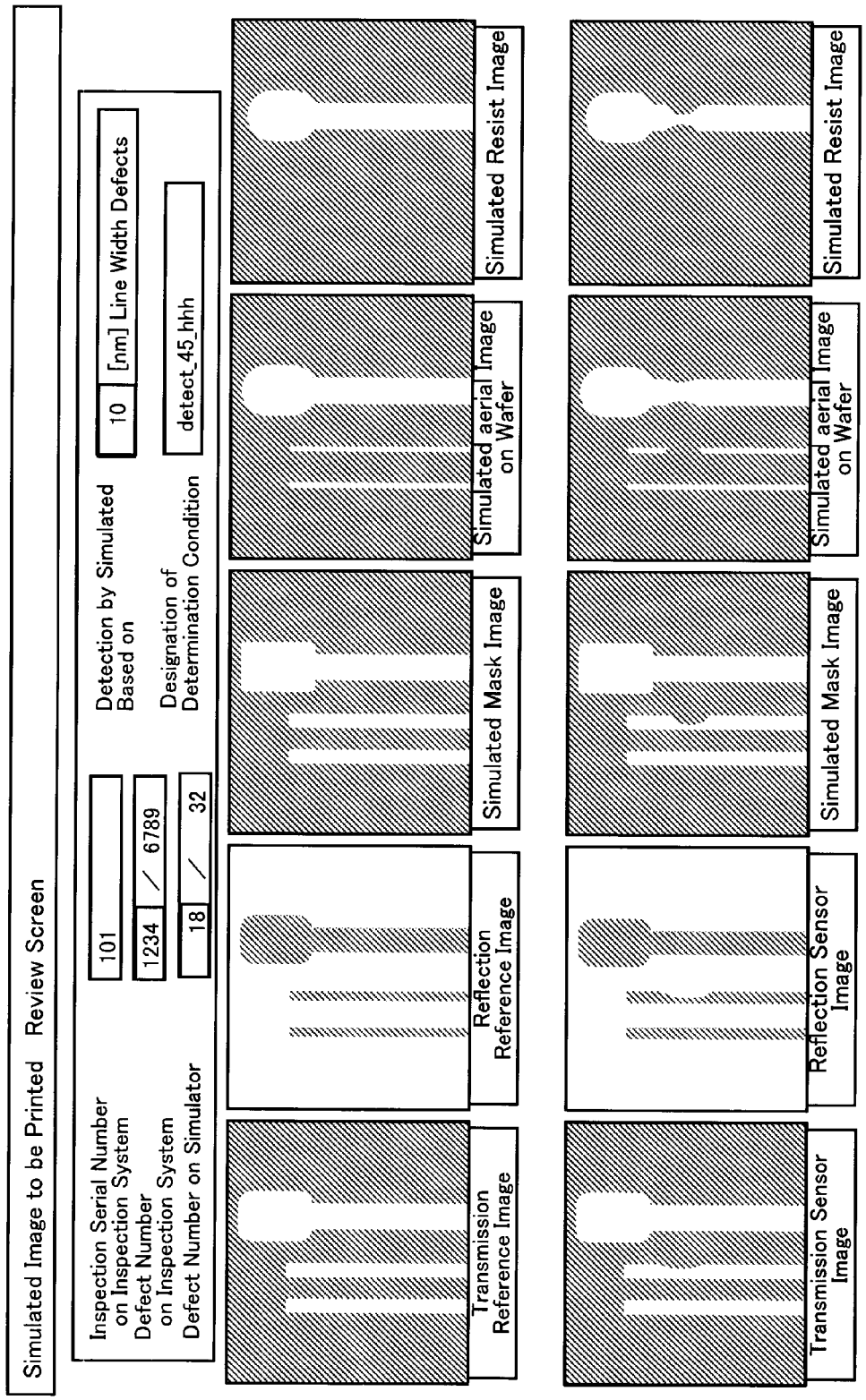
FIG. 8 is an exemplary viewing screen of the results of determining whether a pattern defect on the mask can be tolerated based on simulation results in an embodiment of the present invention.

FIG. 8 shows a screen in which the operator can view the results of determining whether a pattern defect on the mask can be tolerated based on simulation of the aerial image or resist image of a wafer to which the pattern has been printed. Shown in the top row are reference data (or reference images) and simulated images generated based on the reference data (or in the case of die-to-die inspection, sensor images of a reference pattern and simulated images generated based on the sensor images). Shown in the bottom row are sensor images of the pattern having a defect found by the inspection system, and simulated images generated based on the sensor images. Specifically, these images are (from left to right in FIG. 8): (1) an image captured by the transmission optical system of the inspection system, (2) an image captured by the reflection optical system of the inspection system, (3) a mask image generated from these images, (4) a simulated wafer image generated by assuming that the mask image has been printed to a wafer under specified lithography conditions, and (5) a simulated resist image generated by assuming that the resist has specified characteristics.

Figure 9:
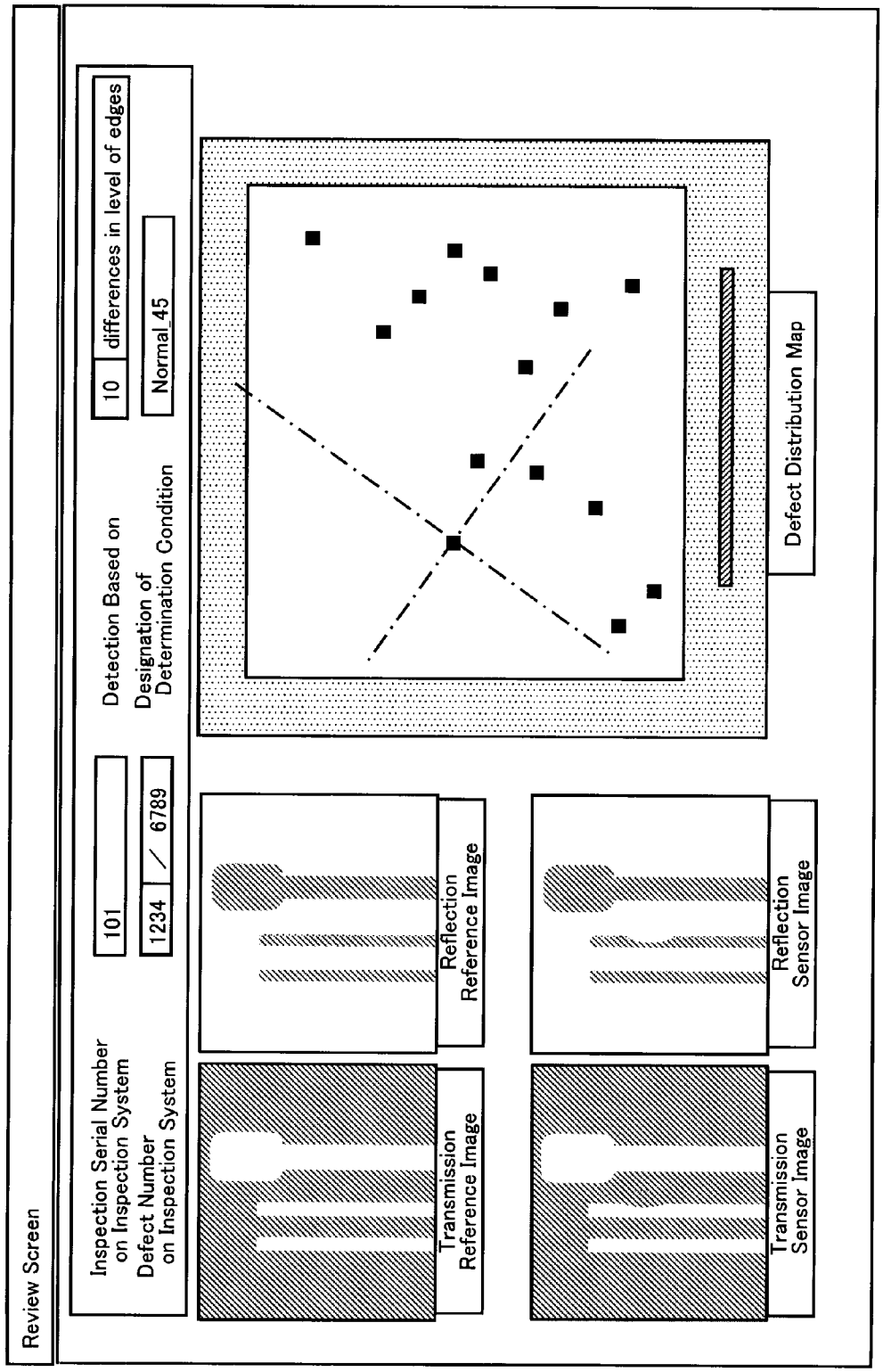
FIG. 9 shows a review screen of a conventional inspection system.

For comparison purposes, FIG. 9 shows a review screen of a conventional inspection system. This screen includes a window for showing sensor images of a pattern having a defect and the reference images which were used to detect the defect, allowing the operation to compare these images. The screen also includes a window for showing defect distribution over an inspection area on the mask. Such a review screen may also include a window for displaying the difference between the sensor images and reference images, a window for dump display of the numerical value of the intensity of each pixel of the sensor images and reference images, and a profile screen window for showing the intensities of sensors disposed in a row along the X or Y direction in order to analyze the defects.

Thus, since the review screen of the present embodiment shown in FIG. 8 shows the first and second inspection results, the operator can compare an optical image of the mask captured by the transmission or reflection optical system of the inspection system, or the corresponding reference image, with a simulated aerial image or resist image of a wafer generated by assuming that the mask image has been printed to the wafer under selected lithography conditions. It should be noted that since the operation results from the lithography simulator are reflected in the second inspection (results), the operator may rely on the second inspection results to select a defect or defects to be further reviewed or inspected.

The review process of the present embodiment should preferably use, in addition to sensor images captured by the inspection system 100, data required for visually recognizing areas of the pattern around defects, which data is extracted from the design pattern data. Such extraction from the design pattern data may be accomplished as follows.

Figure 10C:
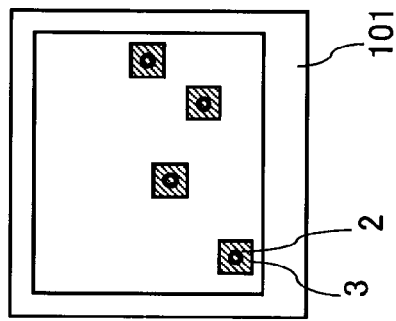
FIG. 10C is a diagram schematically showing extracting data.
Figure 10B:
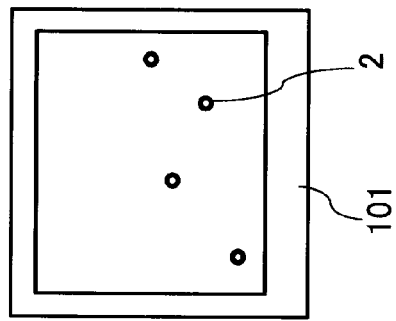
FIG. 10B is a diagram schematically showing defects.
Figure 10A:
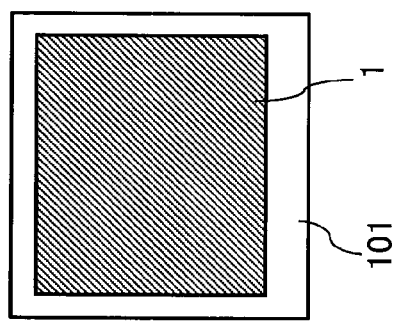
FIG. 10A is a diagram schematically showing a design pattern.

FIG. 10A is a diagram schematically showing a design pattern 1 written on the photomask 101. Further, FIG. 10B is a diagram schematically showing defects 2 detected on the photomask 101. The positions of these defects are defined, e.g., in an XY coordinate system with its origin located at the center of the mask. Further, the pattern data used in die-to-database inspection to generate a reference image, that is, the data shown in FIG. 10A, also describes geometries in the same XY coordinate system with its origin located at the center of the mask. (That is, the design pattern 1 shown in FIG. 10A is also expressed in the same XY coordinate system.) It should be noted that the geometry of the surface of the mask can be expressed in two XY coordinate systems as viewed from the glass surface and the film surface, respectively, of the mask; the positive direction of the X or Y axis of one XY coordinate system is opposite to that of the other (i.e., these XY coordinate systems are mirror images of each other). However, in this example, the coordinate positions of detected defects and the pattern in the database are expressed in the XY coordinate system as viewed from the glass surface of the mask. In accordance with the present embodiment, data required for visually recognizing areas 3 of the pattern around defects is extracted from the design pattern data based on the coordinates of the defects, as shown in FIG. 10C. The design pattern data is defined in a hierarchical structure made up of cluster data or cell data describing clusters or cells each including a group of pattern features. Clusters or cells are grouped into frames or stripes. The data of clusters, cells, frames, and stripes specifies their dimensions and shapes. For example, the data of a cluster specifies its shape (a rectangle), its dimensions, and its reference point (the lower left apex), etc.

The reference pattern image of a defect may extend over a plurality of clusters or cells, and even over a plurality of frames or stripes. Therefore, it is practical that the pattern area to be inspected around the defect (referred to herein as the "defect inspection pattern area") may be specified in the database by specifying a plurality of clusters or cells whose reference points are located less than a predetermined distance away from the position of the defect in the X and Y directions, instead of specifying each pattern feature in the defect inspection pattern area.

The inspection result information, which includes the coordinates of defects, and the design pattern data are stored in the first magnetic disk unit 109a shown in FIG. 1. The data of the defect inspection pattern area for each defect is extracted from the design pattern data as follows. First, the control computer 110 determines the two X coordinate lines a predetermined distance away from the X coordinate line passing through the position of the defect and also determines the two Y coordinate lines a predetermined distance away from the Y coordinate line passing through the position of the defect. The control computer 110 then determines the clusters or cells whose reference points are located within the area defined and enclosed by these determined four coordinate lines, and extracts the data of these clusters or cells from the design pattern data read from the first magnetic disk unit 109a. The control computer 110 then generates an output file containing the extracted data. The output file is converted into the same format as the input design pattern data or into OASIS format, which is highly versatile, before it is stored in the second magnetic disk unit 109b.

Incidentally, although in the example shown in FIG. 7 the inspection system 100 sends information (inspection data) about a mask to the lithography simulator 400 after the completion of the inspection of the mask, it is to be understood that the present embodiment is not limited to this particular method. For example, each time the inspection of the mask has progressed by a predetermined amount, the information obtained during that period may be sent to the lithography simulator 400. The inspection system 100 may be adapted to allow one to select one of these two methods. It should be noted that the above predetermined amount of progress in the inspection may be such that the inspection information is sent each time a predetermined number of stripes (or strip-shaped regions) in the inspection region have been scanned and inspected (where the inspection region is divided into stripes), or each time a predetermined amount of area of the inspection region has been inspected or the number of detected defects has exceeded a predetermined value.

Figure 11:
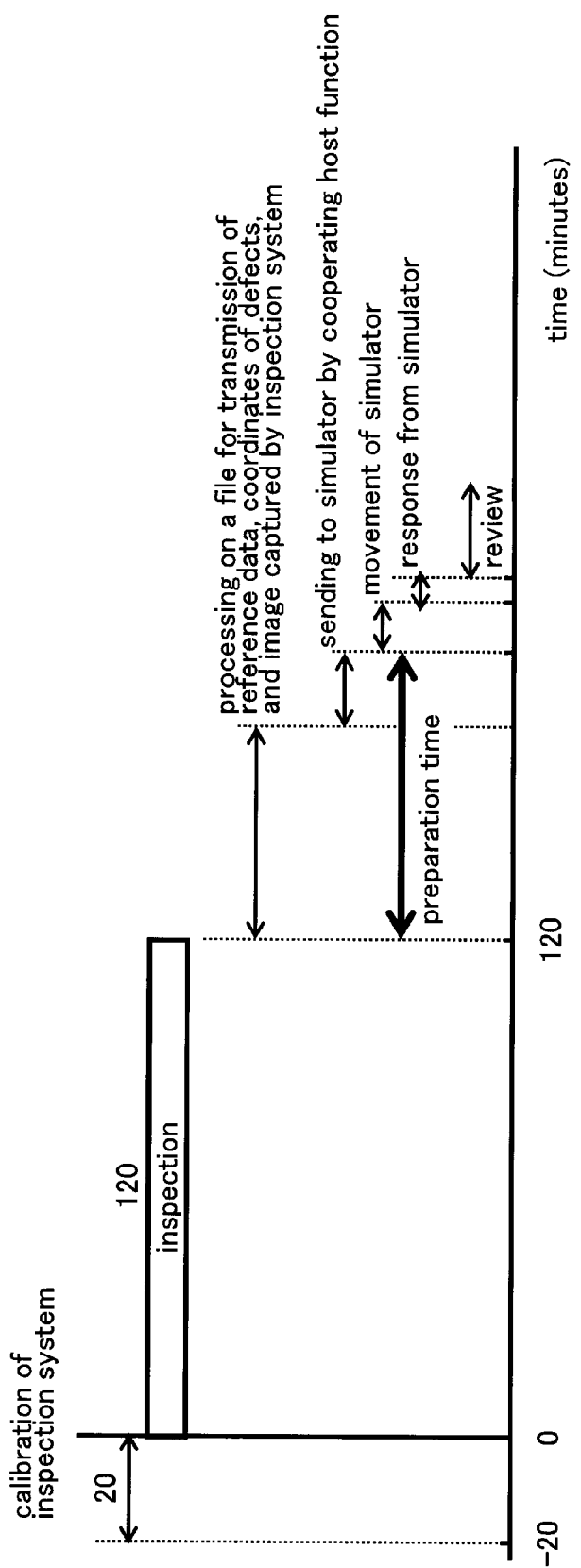
FIG. 11 is an exemplary inspection system sends information about a mask to the lithography simulator after the completion of the inspection of the mask.

In the example shown in FIG. 11, the inspection system 100 sends information about a mask to the lithography simulator 400 after the completion of the inspection of the mask. That is, after the completion of the inspection, the cooperating host function of the control computer 110 operates to send the first inspection results and information required for operation (or simulation) to the lithography simulator.

In the example shown in FIG. 11, the entire surface of the mask is inspected after calibrating the inspection system. Upon completion of this inspection, the control computer performs processing on the file containing the coordinates of the defects found in the inspection so as to be able to transmit it to the lithography simulator. Specifically, the file is converted into XML format. The optical image captured by inspection system 100 is then converted into bitmap data, etc. Further, the control computer 110 reads pattern data (or pattern writing data) from the database, which data is used by the inspection system 100 to generate reference data. The computer then converts the read pattern data into OASIS format, which is highly versatile. These data are stored in the second magnetic disk unit 109b shown in FIG. 1. The control computer 110 then reads the data from the second magnetic disk unit 109b and sends it to the lithography simulator 400 by performing its cooperating host function. The lithography simulator 400 waits and, upon receiving an operation start instruction from the cooperating host function, simulates the aerial image or resist image of a wafer based on the received information. The operation results (or simulated images) from the lithography simulator 400 are sent back to the inspection system 100 through the general communications network and used to produce the second inspection results. The operator then reviews the defects of the pattern based on the first and second inspection results.

Figure 12:
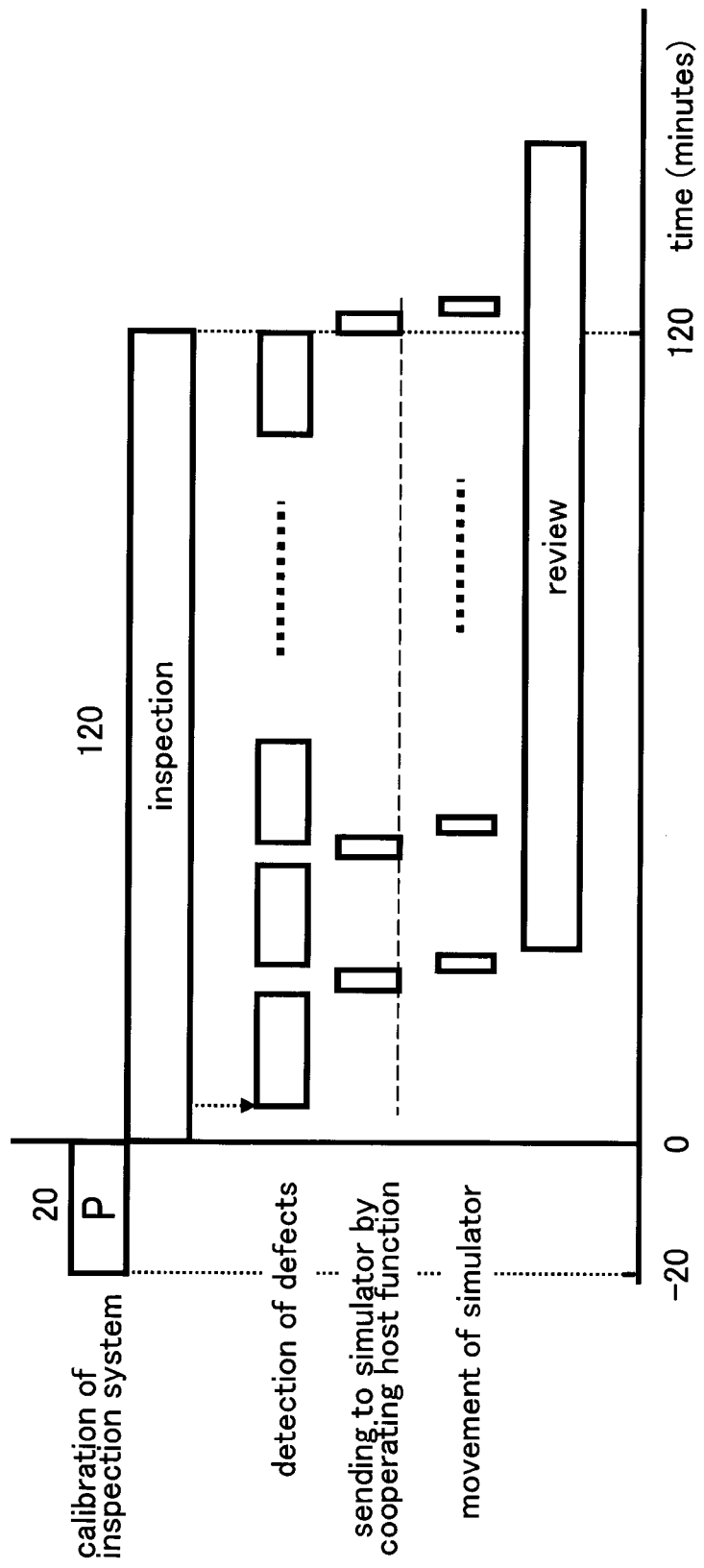
FIG. 12 is an exemplary inspection of the mask has progressed by a predetermined amount, the information obtained during that period is sent to the lithography simulator.

In the example shown in FIG. 12, each time the inspection of the mask has progressed by a predetermined amount, the information obtained during that period is sent to the lithography simulator 400. That is, during the inspection, the cooperating host function of the control computer 110 operates to send the first inspection results and information required for operation (or simulation) to the lithography simulator.

In the example shown in FIG. 12, the entire surface of the mask is inspected after calibrating the inspection system. When the number of detected defects has reached a predetermined value, the control computer 110 converts information such as the coordinates of the defects and the optical image captured by the inspection system into an appropriate data format, as in the example shown in FIG. 11, and the cooperating host function of the control computer 110 sends it to the lithography simulator 400. Upon receiving an operation start instruction from the cooperating host function, the lithography simulator 400 simulates the aerial image or resist image of a wafer based on the received information. The operation results (or simulated images) from the lithography simulator 400 are sent back to the inspection system 100 through the general communications network and used to produce the second inspection results. The operator then reviews the defects of the pattern based on the first and second inspection results. The surface of the mask is still further inspected during this series of operations, and when the number of newly detected defects has reached a predetermined value, the control computer 110 sends the obtained data to the lithography simulator 400, which then simulates the aerial image or resist image of a wafer and sends the operation results (or simulated images) to the inspection system 100, where the operator then reviews the defects, as in the above inspection cycle. This series of operations is repeated until the inspection of the entire mask surface has been completed.

Figure 13:
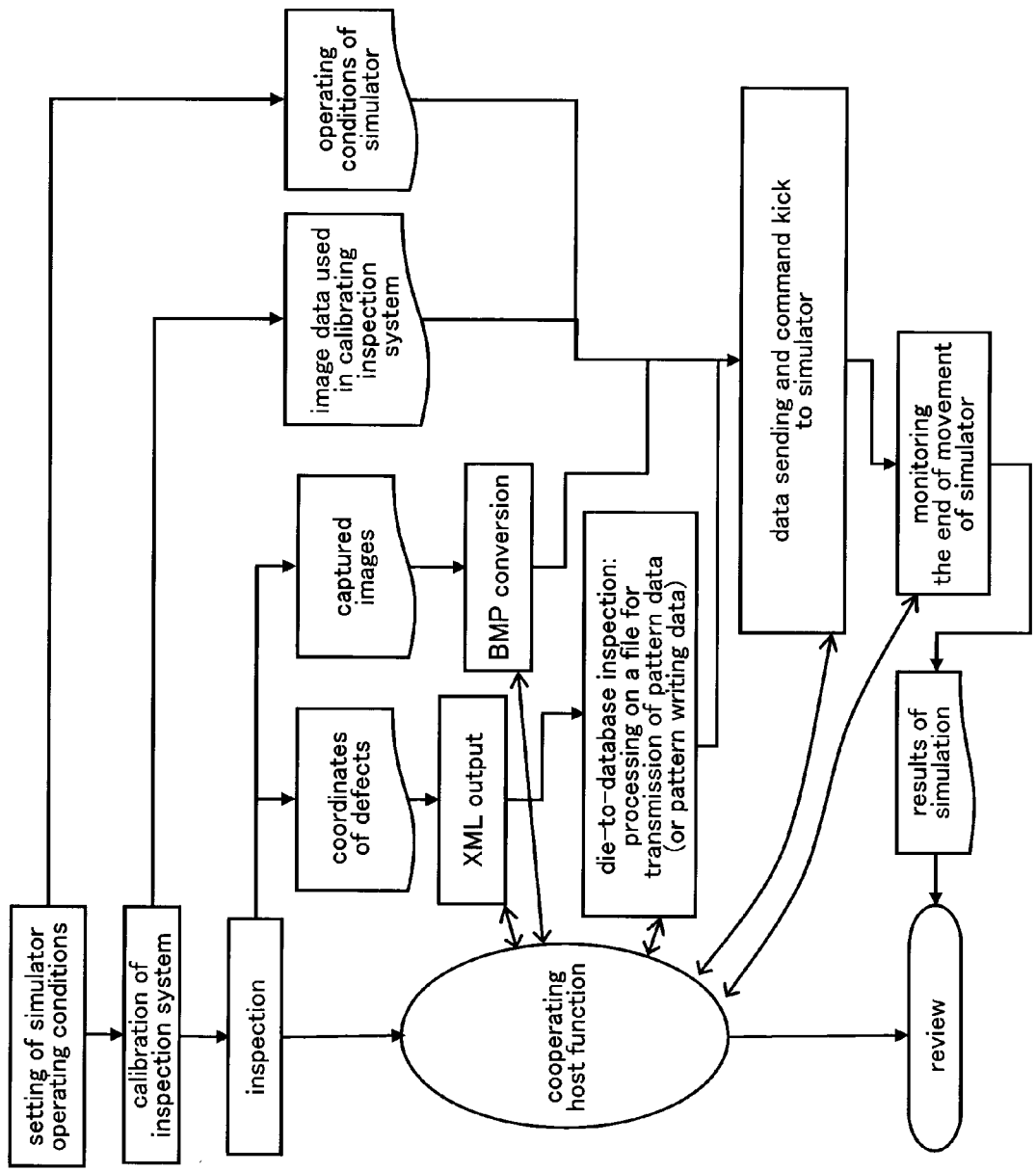
FIG. 13 is an exemplary flowchart of the inspection method of the present embodiment.

FIG. 13 is an exemplary flowchart of the inspection method of the present embodiment.

In this method, for example, data and parameters of the lithography simulator 400 are set in the operation setting screen (as shown in FIG. 7) of the control computer 110 in the inspection system 100. Next, the entire surface of the mask is inspected after calibrating the inspection system 100. The coordinates of the defects found in the inspection are written in an XML file. Further, when the inspection system 100 is in the die-to-database inspection mode, the control computer 110 reads pattern data (or pattern writing data) from the database, which data is used by the inspection system 100 to generate reference data. The computer then converts the read pattern data into OASIS format, which is highly versatile. The optical image captured by the inspection system 100, on the other hand, is converted into a bitmap (BMP conversion). These data are sent to the lithography simulator 400, together with simulation operating conditions and the image data that was used to calibrate the inspection system 100. Upon receiving an operation start instruction from the cooperating host function, the lithography simulator 400 starts its operation. When the lithography simulator 400 has completed its operation, the cooperating host function is notified, and the operation results are sent to the inspection system 100. The operator then reviews the defects.

As described above, the inspection system of the present invention has an interface unit through which data can be exchanged with a lithography simulator. This allows the lithography simulator to perform an operation (or simulation) based on the first inspection results produced by the inspection system. Further, the operation results from the lithography simulator can be sent to the inspection system. The operator can review the defects based on the first inspection results and the results of the second inspection in which the operation results from the lithography simulator are reflected. Therefore, the operator can rely on the second inspection results to select a defect or defects to be further reviewed or inspected, making it easy to determine whether defects can be tolerated. Further in accordance with the present invention, the inspection system does not include a simulator and is adapted to use a lithography simulator which is an external device, meaning that the inspection system can be combined with any lithography simulator suitable for the application intended. Thus, the inspection system of the present invention can work in conjunction with any suitable lithography simulator and therefore may be combined with a highly versatile simulator.

For example, the inspection system of the present embodiment may be connected through a network to other systems and apparatuses, e.g., to one or more other inspection systems, a plurality of lithography simulators, and a mask repair system. In the manufacture of masks in which a plurality of inspection systems are used, the inspection system that produces first inspection results and sends them to the lithography simulator is not necessarily the same as the inspection system that receives the operation results from the lithography simulator and produces second inspection results. When the inspection system that produces the first inspection results is different from the inspection system that produces the second inspection results, these inspection systems may be designed to exchange data such as the inspection results and the operation results from the lithography simulator through a network such as Ethernet©.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all pattern inspection systems and pattern inspection methods employing the elements of the invention and variations thereof which can be designed by those skilled in the art.

The features and advantages of the present invention may be summarized as follows.

The inspection system of the present invention is capable of facilitating defect evaluation and capable of performing a defect evaluation process in conjunction with a highly versatile simulator.

Obviously many modifications and variations of the present invention are possible in the light of the above teachings. It is therefore to be understood that within the scope of the appended claims the invention may be practiced otherwise than as specifically described.

The entire disclosure of a Japanese Patent Application No. 2009-189605, filed on Aug. 18, 2009 including specification, claims, drawings and summary, on which the Convention priority of the present application is based, are incorporated herein by reference in its entirety.

What is claimed is:

1. An inspection apparatus comprising:
   an optical image capture unit configured to capture optical images of an object to be inspected by irradiating the object with light;
   a comparing unit configured to compare a first optical image with reference information to determine coordinates of a portion of the first optical image determined to be a defect, wherein the first optical image and the coordinates of the portion together form a first inspection result; and
   an interface unit configured to output to a lithography simulator the first optical image and the coordinates,
   wherein the interface unit is connected to the lithography simulator through a general communications network and is configured to instruct the lithography simulator to generate a first simulated image of the portion of the first optical image, generate a second simulated image using the reference information, compare the first and second simulated images, identify a defect if a difference between the first and second simulated images exceeds a predetermined threshold, and send a result of the comparison to the comparing unit; and
   wherein the comparing unit is configured to inspect a second optical image different from the first optical image selected based upon the result of the comparison and produce a second inspection result, and configured to display the first and second inspection results.

2. The inspection apparatus according to claim 1, wherein the object to be inspected is divided into stripes to continuously acquire the first optical image; and
   the first inspection result is sent from the interface unit to the lithography simulator when inspection of a predetermined number of stripes is completed.

3. An inspection apparatus comprising:
   an optical image capture unit configured to capture a first optical image of an object to be inspected by irradiating the object with light;
   a reference image generating unit configured to generate a first reference image from design data of the object to be inspected;
   a comparing unit configured to compare the first optical image with the first reference image to determine coordinates of a portion of the first optical image determined to be a defect, wherein a second reference image is newly generated from the design data and coordinates of a portion of the first optical image determined to be a defect by the comparison, and wherein the first optical image, the second reference image, and the coordinates of the portion together form a first inspection result; and
   an interface unit configured to output to a lithography simulator the first optical image, the second reference image newly generated from the design data, and the coordinates of the portion determined to be a defect by the comparison, and instruct the lithography simulator to produce simulated images from the first optical image and the second reference image, compare the simulated images, and identify a defect based upon the comparison of the simulated images, wherein the comparing unit is configured to inspect a second optical image different from the first optical image selected based upon the comparison of the simulated images and produce a second inspection result, and configured to display the first and second inspection results; and wherein the interface unit is connected to the lithography simulator through a general communications network.

4. The inspection apparatus according to claim 3, wherein the second reference image is prepared by extracting data from the design data, the extracted data being required to visually recognize a pattern around the portion determined to be the defect.

5. The inspection apparatus according to claim 3, wherein the object to be inspected is divided into stripes to continuously acquire the optical image; and the first inspection result is sent from the interface unit to the lithography simulator when inspection of a predetermined number of stripes is completed.

6. An inspection apparatus comprising:

an optical image capture unit configured to capture a first optical image of an object to be inspected by irradiating the object with light; and an inspection unit configured to inspect the first optical image by comparing the first optical image with reference information to determine coordinates of a portion of the first optical image determined to be a defect, wherein the first optical image and the coordinates of the portion together form a first inspection result; and an interface unit connected to a lithography simulator through a general communications network, wherein:

the inspection unit is configured to output to the lithography simulator the first optical image, the reference information and the coordinates when a predetermined number of defects are found, using the interface unit, before inspection of the first optical image is completed;

the interface unit is configured to instruct the lithography simulator to generate a first simulated image of the portion of the first optical image, generate a second simulated image using the reference information, compare the first and second simulated images, identify a defect if a difference between the first and second simulated images exceeds a predetermined threshold, and send results of the comparison to the inspection unit; and the inspection unit is configured to produce a second inspection result using the first inspection result and the results of the lithography simulator and to display the first and second inspection results.

* * * * *

UNITED STATES PATENT AND TRADEMARK OFFICE
CERTIFICATE OF CORRECTION

PATENT NO. : 9,031,313 B2  Page 1 of 1
APPLICATION NO. : 12/781232
DATED : May 12, 2015
INVENTOR(S) : Hideo Tsuchiya et al.

It is certified that error appears in the above-identified patent and that said Letters Patent is hereby corrected as shown below:

On the title page, Item (73), the Assignees' Information is incorrect. Item (73) should read:

--(73) Assignees: NuFlare Technology, Inc., Numazu-shi (JP);
Kabushiki Kaisha Toshiba, Tokyo (JP);
NEC Corporation, Tokyo (JP)--

Signed and Sealed this
Twenty-second Day of September, 2015

Michelle K. Lee
*Director of the United States Patent and Trademark Office*